United States Patent [19]

Miller et al.

[11] Patent Number: 5,516,961
[45] Date of Patent: *May 14, 1996

[54] DEHYDROGENATION USING SULFUR TOLERANT ZEOLITE CATALYST

[75] Inventors: Stephen J. Miller, San Francisco; Paul G. Johnson, Pinole, both of Calif.

[73] Assignee: Chevron U.S.A. Inc., San Francisco, Calif.

[*] Notice: The term of this patent shall not extend beyond the expiration date of Pat. No. 5,358,631.

[21] Appl. No.: 252,705

[22] Filed: Jun. 2, 1994

Related U.S. Application Data

[60] Division of Ser. No. 991,872, Dec. 16, 1992, which is a continuation-in-part of Ser. No. 902,987, Jun. 23, 1992, Pat. No. 5,358,631, which is a division of Ser. No. 488,332, Mar. 2, 1990, Pat. No. 5,169,813.

[51] Int. Cl.⁶ ................................................... C07C 5/33
[52] U.S. Cl. .................... 585/660; 502/64; 502/66; 585/654; 585/659
[58] Field of Search ..................... 502/64, 66, 77, 502/53, 56, 906; 585/655, 659, 660, 906

[56] References Cited

U.S. PATENT DOCUMENTS

| | | | |
|---|---|---|---|
| 5,052,561 | 10/1991 | Miller et al. | 208/137 |
| 5,169,813 | 12/1992 | Miller et al. | 502/66 |
| 5,182,012 | 1/1993 | Miller et al. | 208/137 |

Primary Examiner—E. Rollins Cross
Assistant Examiner—B. Yildirim
Attorney, Agent, or Firm—R. J. Sheridan

[57] ABSTRACT

A process is provided for catalyst dehydrogenation of light paraffinic hydrocarbons using a catalyst comprising a noble metal and an intermediate pore size zeolite having a specified alkali content. The catalyst is sulfur tolerant, so that the dehydrogenation process can be carried out in the presence of sulfur or with periodic exposure to sulfur.

40 Claims, No Drawings

DEHYDROGENATION USING SULFUR TOLERANT ZEOLITE CATALYST

This is a divisional of application Ser. No. 07/991,872, filed Dec. 16, 1992 which is a continuation-in-part of Ser. No. 902,987, filed Jun. 23, 1992, now U.S. Pat. No. 5,358,631 which is a division of Ser. No. 488,332, filed Mar. 2, 1990, now U.S. Pat. No. 5,169,813.

BACKGROUND OF THE INVENTION

The present invention relates to dehydrogenation using a catalyst containing a crystalline zeolite. Dehydrogenation is a well-known reaction wherein paraffins are converted to olefins. With $C_6^+$ hydrocarbons, dehydrogenation is generally accompanied by dehydrocyclization and aromatization reactions. With $C_2$–$C_5$ alkanes, dehydrogenation reactions follow different reaction pathways, depending on molecular type. Reaction equilibrium reflect these differences in reaction pathways. It is important, therefore, to provide a catalyst and process conditions specifically for the dehydrogenation of a light paraffinic hydrocarbon feed.

The catalyst of the present invention is a dehydrogenation catalyst comprising a zeolite, and having therein a specific quantity of alkali and/or alkaline earth components. Dehydrogenation catalysts containing alkali or alkaline earth components are known. In C. N. Satterfield, *Heterogeneous Catalysis in Practice,* New York: McGraw-Hill Book Company, 1980, p. 269, an $Fe_2O_3$—$Cr_2O_3$—$K_2CO_3$ butene dehydrogenation catalyst is described, in which the potassium component helps to maintain catalyst activity by promoting the reaction between steam in the feed and coke deposited on the catalyst.

U.S. Pat. No. 4,124,649 to Rausch discloses a porous, non-acidic carrier material containing a platinum or palladium component, a rhodium component, and a tin component for use in dehydrogenation. The non-acidic carrier material contains about 0.1 to about 5 wt. % of an alkali metal or alkaline earth metal. Lithium and potassium are preferred. It is taught that the function of the alkali/alkaline earth component is to neutralize any of the acidic material which may have been used in the preparation of the dehydrogenation catalyst.

U.S. Pat. No. 4,438,288 to Imai and Hung describes a dehydrogenation catalyst containing a platinum group component, a porous support material, and an excess of an alkali or alkaline earth component relative to the platinum group component. This catalyst is taught as being particularly useful for dehydrogenating paraffins having from 2 to 5 or more carbon atoms to the corresponding mono-olefins or for dehydrogenating mono-olefins having 3 to 5 or more carbon atoms to the corresponding di-olefins.

Crystalline molecular sieve zeolites have also been disclosed for dehydrogenation of paraffinic hydrocarbons. As with the art cited above, which teaches the use of a non-crystalline dehydrogenation catalyst, the acidity of the zeolitic-containing dehydrogenation catalysts is an important variable. For example, U.S. Pat. No. 4,665,267 and U.S. Pat. No. 4,795,732, both to Barri teach using a catalyst having a silicalite support and containing a platinum group metal for the dehydrogenation of $C_2$ to $C_{10}$ paraffins. The catalyst of Barri is substantially free of alkali and alkaline earth metals.

U.S. Pat. No. 4,401,555 to Miller is directed to olefin production from paraffins using silicalite having a low sodium content. The silicalite used in the '555 process contains less than 0.1 wt. % sodium and is composited in a matrix which is substantially free of cracking activity. Also, the composite has no hydrogenation component. According to the '555 process, the paraffinic feed may be hydrotreated to reduce sulfur levels to less than 100 ppm organic sulfur.

An intermediate pore size crystalline silicate having a high silica to alumina ratio, a relatively low alkali content, and a small crystallite size is taught as a sulfur tolerant reforming or dehydrocyclization catalyst in International Patent Application WO91/13130.

Other non-acidic catalysts have been proposed for dehydrogenation of paraffins. In U.S. Pat. No. 4,962,250, an non-acidic MCM-22 zeolite, in combination with a Group VIII metal species, is taught for dehydrogenation of $C_2$–$C_{12}$ aliphatic hydrocarbons. In order to be non-acidic, the '250 reference teaches that the finished catalyst should contain cation equivalents of Group IA and/or IIA cations equal to or greater than the framework aluminum content.

In U.S. Pat. No. 4,929,792 to Dessau, a zeolite Beta in non-acidic form is disclosed for dehydrogenation of a $C_2$–$C_{12}$ paraffin containing feed. To render the Beta zeolite non-acidic, '792 teaches titrating the zeolite with Group IA or IIA in ion-exchangeable form until a pH of greater than 7 is achieved.

While the patents cited above disclose modifying the acidity of a dehydrogenation catalyst, they do not recognize the importance of adding a specific quantity of alkali component to the dehydrogenation catalyst. In particular, sufficient alkali is important for suppressing undesirable cracking reactions, for increasing reaction selectivity, and for increasing yield of the desired product. On the other hand, excessive amounts of alkali decreases the sulfur resistance of a dehydrogenation catalyst which contains a crystalline zeolite. The process of the present invention provides a catalyst having a specific quantity of an alkali component for high activity, high selectivity, and high stability.

SUMMARY OF THE INVENTION

Accordingly, a process is provided for dehydrogenating a light paraffinic hydrocarbon stream using a catalyst with high selectivity and low deactivation rate. More specifically, a process is provided for dehydrogenating a light paraffinic hydrocarbon feed in a reaction zone which may be subjected to periodic exposure to more than 100 ppb sulfur, which process comprises contacting the feed under catalytic dehydrogenation conditions with a catalyst comprising:

(a) a noble metal;

(b) an intermediate pore size zeolite having a silica to alumina ratio of at least about 30, preferably at least about 200; and more preferably at least about 500; and (c) an alkali content wherein the alkali to aluminum ratio in the zeolite is between about 1 and about 5, and preferably between about 1 and about 3, on a molar basis.

The alkali content is of great importance in the present invention. Among other factors, the present invention is based on our finding that the dehydrogenation catalyst of the present process, when treated with a specific amount of an alkali and/or alkaline earth component, has a surprisingly low deactivation or fouling rate and a surprisingly high selectivity and activity for dehydrogenation. It has also been found that such low fouling rates are achieved even after sulfur breakthrough or other periodic exposure of the dehydrogenation catalyst to sulfur. Fouling or deactivation rate is the rate at which the dehydrogenation zone reaction temperature needs to be raised per unit time, e.g., ° F. per hour, in order to maintain a given feed conversion.

We have further found that it is advantageous to sulfide the catalyst used in the present invention. The sulfiding can be done by known presulfiding techniques, for example, by passing a gas stream containing hydrogen sulfide over the catalyst prior to commencing the dehydrogenation run, or the sulfiding of the catalyst can be carried out through the sulfur in the feed to the process. We have found that, in catalytic dehydrogenation, the combination of a specific alkali level in the intermediate pore size zeolite of high silica to alumina ratio and sulfiding of the catalyst allows the achievement of surprisingly good olefin yields, high selectivity to olefins and low fouling rates even after exposure to sulfur.

We have found that, for the catalyst used in the process of the present invention, it is advantageous to use small crystallite size intermediate pore size zeolite of high silica to alumina ratio. Small crystallite size for this component of the catalyst is discussed in more detail in co-assigned U.S. Pat. No. 5,052,561, issued Oct. 1, 1991, and titled "A Crystalline Silicate Catalyst and a Reforming Process Using the Catalyst". The disclosure of U.S. Pat. No. 5,052,561 is incorporated herein by reference, particularly its disclosure with regard to small crystallite size intermediate pore size zeolite and methods of making such crystallites. Preferred small crystallite sizes for the present invention are less than 10 microns, more preferably less than 5 microns, still more preferably less than 2 microns, and especially preferred less than 1 micron. The size is on a basis of the largest dimension of the crystallites. Preferred shapes for the crystallites are approximately spherical. When a crystallite size is specified, preferably at least 70 wt. % of the crystallites are within the specified range, more preferably at least 80 wt. %, and most preferably at least 90 wt. %.

Thus, according to a preferred embodiment of the present invention, the catalyst used in the dehydrogenation process comprises an intermediate pore size zeolite of small crystallite size and having a high silica to alumina ratio with a specific alkali content. According to a particularly preferred embodiment, the catalyst is presulfided or is sulfided during dehydrogenation operations.

The zeolite component of the catalyst of the present invention is generally referred to herein as zeolite, but also is commonly referred to as a crystalline silicate or silicate.

The term "alkali" is used herein to mean Group IA metals. Preferred alkali metals for use in the catalyst of the present invention are sodium, potassium, cesium, lithium and rubidium. Sodium and potassium are more preferred. Sodium is the most preferred alkali metal for use in the catalyst.

The amount of alkali must be lower than the levels typically taught in the prior art for "non-acidic" catalyst. The amount of alkali will vary depending on the ratio of silica to alumina in the zeolite component of the catalyst, with less alkali being required as the silica to alumina ratio of the zeolite increases. Preferred alkali amounts, where the alkali is sodium, for example, for the catalyst where the silica to alumina ratio is 500:1 are about 750 ppm to about 3800 ppm.

Amounts of alkali are by weight based on the total weight of the zeolite component of the catalyst. The abbreviation ppm indicates parts per million.

The amount of alkali is an amount sufficient to neutralize substantially all of the acidity of the zeolite. Preferred amounts of alkali are between one and five parts alkali to one part aluminum, more preferably between one and three parts alkali to one part aluminum on a molar basis, based on the aluminum in the zeolite. Thus, the amount of alkali will vary as a function of aluminum. Typical preferred lower amounts of alkali are 0.01, more typically 0.1 wt. %. In most cases, some alkali is present in the zeolite that cannot be readily ion exchanged out of the silicate on a practical basis. This difficult to exchange alkali can be minimized by selecting appropriate methods of preparing the silicate, for instance, as disclosed in Example 1 hereinbelow.

The zeolite of the catalyst of the present invention preferably is low in acidity, more preferably substantially free of acidity. However, the low acidity zeolite, or zeolite substantially free of acidity, is, in accordance with the present invention, not achieved by using large amounts of alkali. The low acidity, or substantial non-acidity, may be achieved by a combination of low aluminum content in the zeolite and the use of low amounts of alkali and/or the use of alkaline earth metals. The silicate component of the catalyst preferably is included in a matrix or binder to form the finished catalyst, as described hereinbelow. Preferably, the finished catalyst is of low acidity, more preferably substantially free of acidity.

The acidity of the zeolite may be determined as follows: 0.1–1.5 g of zeolite is mixed with 1 g of acid-washed and neutralized alundum and packed in a 3/16" stainless steel reactor tube with the remaining space filled with alundum. The reactor contents are calcined for one hour at 450° C. The reactor is then placed in a clam-shell furnace at 427° C. and the reactor outlet connected to the inlet of a gas chromatograph. The inlet is connected to the carrier gas line of the GC. Helium is passed through the system at 30 cc/min. 0.04 Microliter pulses of n-decane are injected through a septum above the reactor and reaction products are determined by standard GC analysis. Blank runs with alundum should show no conversion under the experimental conditions, nor should a 100% Catapal alumina catalyst.

A pseudo-first-order, cracking rate constant, k, is calculated using the formula:

$$k = \frac{1}{A} \ln \frac{1}{1-x}$$

where A is the weight of silicate in grams and x is the fractional conversion to products boiling below decane. The silicate is substantially free of acidity when the value of ln k is less than about −3.8. The silicate is low in acidity if ln k is less than about −2.3.

The zeolite as described below, may be a component of the final catalyst, for instance where the final catalyst is a zeolite "bound" in a matrix such as silica or alumina. In such case, the zeolite acidity should be determined by measuring acidity of the zeolite as a separate component.

The acidity of the finished catalyst containing the zeolite may also be assessed as described above.

In accordance with an alternate preferred embodiment of the present invention, an alkaline earth metal (Group IIA metal) is also included in the catalyst. Magnesium, calcium, strontium and barium are preferred Group IIA metals. Magnesium is a more preferred Group IIA metal for use in the catalyst of the present invention. The alkaline earths are advantageously used to reduce the acidity of the catalyst. The alkaline earth metals are not as effective as the alkali metals in reducing acidity, but we have found that the alkaline earth metals do not impart as much sulfur sensitivity to the catalysts as do the alkali metals. In this preferred alternate embodiment, alkaline earth metals are included in the zeolite in an amount between 0.1 to 10.0, preferably 0.5 to 5.0, parts of alkaline earth metal per part alkali metal, on a molar basis.

Additionally, the acid sites can advantageously be neutralized with other basic components such as cerium or lanthanum.

An important aspect of the present invention is the sulfur tolerance of the catalyst. Sulfur tolerance is used herein primarily to connote that the catalyst may be exposed to substantial amounts of sulfur, such as more than 2 ppm sulfur, and return to relatively high activity after the exposure to high sulfur levels is discontinued. We have also found that the catalyst of the present invention has a surprising resistance to sulfur poisoning or deactivation in the range of about 0.1 to 2 ppm sulfur. Thus, in addition to the catalyst capability of "bouncing back" in activity after discontinuance of sulfur in the feed, the catalyst also can "resist" or tolerate, as a steady component in the feed, up to 2 ppm sulfur, more preferably up to 1 ppm sulfur, most preferably up to 0.5 ppm sulfur. Accordingly, the terminology "sulfur tolerance" is used herein to embrace the catalyst's capability to regain activity after discontinuance of exposure to sulfur and also the catalyst's ability to perform well (low fouling rate and good activity) in the presence of moderate amounts of sulfur.

The sulfur tolerance can be utilized in various ways. The feed to the process may contain relatively high amounts of sulfur compared to feed to other catalytic dehydrogenation processes using zeolitic-based catalysts, or the feed may be subject to periodic exposure to high amounts of sulfur (and hence the dehydrogenation zone subject to periodic high amounts of sulfur).

By "periodic exposure" is meant sulfur increases in the feed and hence in the dehydrogenation zone, for example, due to upsets in desulfurization steps upstream of the catalytic dehydrogenation zone, or breakthroughs or notable rises in the amount of sulfur in the feed due to the upstream sulfur removal steps, or simply due to changes in the base feedstock to the refinery or catalytic dehydrogenation zone. "Periodic" exposure is used to connote exposure to the specified sulfur levels for a significant period of time as opposed to continuous exposure to sulfur. A significant period of time would typically be at least 2 minutes, more typically an hour or more.

When dehydrogenation is carried out using a highly sulfur sensitive zeolite catalyst, it is necessary to go to substantial expense to reduce the sulfur in the feed to very low levels. Frequently, extensive guard bed and/or sulfur sorbent systems are used. Even in a situation where the sulfur content of the feed to the dehydrogenation zone will normally be very low, the catalyst of the present invention is advantageously used as the present catalyst will tolerate exposure to sulfur; that is, the catalyst shows much better activity restoration upon discontinuing the exposure to high sulfur levels. Thus, when using the catalyst of the present invention, the capital cost of a dehydrogenation unit can be reduced, as less sulfur guard or sulfur removal equipment is needed to protect the catalytic dehydrogenation zone as is the case with other zeolite catalysts.

Although the process Of the present invention is found to be a sulfur tolerant process, nonetheless, it is preferred not to subject the catalyst in the dehydrogenation zone to gross amounts of sulfur. Thus, preferably the sulfur in the feed is not above about 25 ppm, more preferably not above 10 ppm, and most preferably not above about 2 ppm. Especially preferred sulfur levels are between 0.1 and 1 ppm.

Amounts of sulfur are by weight based on the feed hydrocarbon to the process. Also, the sulfur is calculated on the basis of elemental sulfur, although the sulfur may be in the form of organic sulfur compounds or in the form of hydrogen sulfide.

Preferred feeds for the dehydrogenation process of the present invention include light alkane or paraffine rich streams containing $C_2$–$C_5$, and preferably $C_3$ and $C_4$ alkanes. For example, a preferred feed is a paraffine rich raffinate obtained from solvent extraction or molecular sieve extraction of paraffins from a mixture of paraffins and aromatics. Another preferred feed is a light distillate stream from a fluid catalytic cracker which is rich in $C_5$ paraffins.

The present invention is directed to a dehydrogenation process as set forth herein. In addition, the present invention is directed to the catalyst, described herein, useful in those processes.

DETAILED DESCRIPTION OF THE INVENTION

As previously described, the present invention uses a ZSM-5 Type intermediate pore size zeolite material. ZSM-5 and ZSM-11 are examples of a ZSM-5 type zeolite. One preferred material is silicalite or very high ratio silica to alumina form of ZSM-5.

Table 1 below reports the X-ray diffraction pattern for ZSM-5 as given in the Argauer patent (U.S. Pat. No. 3,702,886).

TABLE 1

| Interplanar Spacing d(A) | Relative Intensity |
| --- | --- |
| 11.1 ± 0.2 | s. |
| 10.0 ± 0.2 | s. |
| 7.4 ± 0.15 | w. |
| 7.1 ± 0.15 | w. |
| 6.3 ± 0.1 | w. |
| 6.04 } ± 0.1<br>5.97 | w. |
| 5.56 ± 0.1 | w. |
| 5.01 ± 0.1 | w. |
| 4.60 ± 0.08 | w. |
| 4.25 ± 0.08 | w. |
| 3.85 ± 0.07 | v.s. |
| 3.71 ± 0.05 | s. |
| 3.04 ± 0.03 | w. |
| 2.99 ± 0.02 | w. |
| 2.94 ± 0.02 | w. |

Also as reported in the Argauer patent, the values in Table 1 were determined by standard techniques. The radiation was the K-alpha doublet of copper, and a scintillation counter spectrometer with a strip chart pen recorder was used. The peak heights, I, and the positions as a function of 2 times theta, where theta is the Bragg angle, were read from the spectrometer chart. From these, the relative intensities, 100 $I/I_o$, where $I_o$ is the intensity of the strongest line or peak, and d (obs.), the interplanar spacing in A, corresponding to the recorded lines, were calculated. In Table 1, the relative intensities are given in terms of the symbols s.=strong, m.=medium, m.s.=medium strong, m.w.=medium weak and v.s.=very strong. It should be understood that this X-ray diffraction pattern is characteristic of all the species of ZSM-5 compositions. Ion exchange of the sodium ion with cations reveals substantially the same pattern with some minor shifts in interplanar spacing and variation in relative intensity. Other minor variations can occur depending on the silicon to aluminum ratio of the particular sample, as well as if it had been subjected to thermal treatment.

ZSM-5 is regarded by many to embrace "silicalite" as disclosed in U.S. Pat. No. 4,061,724 to Grose et al. For ease of reference herein, silicalite is referred to as a ZSM-5-type material with a very high silica to alumina ratio and is regarded as embraced within the ZSM-5 X-ray diffraction pattern. The silica to alumina ratio is on a molar basis of silica ($SiO_2$) to alumina ($Al_2O_3$).

Various references disclosing silicalite and ZSM-5 are provided in U.S. Pat. No. 4,401,555 to Miller. These references include the aforesaid U.S. Pat. No. 4,061,724 to Grose et al.; U.S. Pat. No. Res. 29,948 to Dwyer et al.; Flanigen et al., Nature, 271, 512–516 (Feb. 9, 1978) which discusses the physical and adsorption characteristics of silicalite; and Anderson et al., J. Catalysis 58, 114–130 (1979) which discloses catalytic reactions and sorption measurements carried out on ZSM-5 and silicalite. The disclosures of these references and U.S. Pat. No. 4,401,555 are incorporated herein by reference, particularly including their disclosures on methods of making high silica to alumina zeolites having an X-ray diffraction pattern in substantial accord with Table 1.

Other zeolites which can be used in the process of the present invention include those as listed in U.S. Pat. No. 4,835,336; namely: ZSM-11, ZSM-12, ZSM-22, ZSM-23, ZSM-35, ZSM-38, ZSM-48, and other similar materials.

ZSM-5 is more particularly described in U.S. Pat. No. 3,702,886 and U.S. Pat. No. Res. 29,948, the entire contents of which are incorporated herein by reference.

ZSM-11 is more particularly described in U.S. Pat. No. 3,709,979 the entire contents of which are incorporated herein by reference. Bibby et al., Nature, 280, 664–665 (Aug. 23, 1979) reports the preparation of a crystalline silicate called "silicalite-2".

ZSM-12 is more particularly described in U.S. Pat. No. 3,832,449, the entire contents of which are incorporated herein by reference.

ZSM-22 is more particularly described in U.S. Pat. Nos. 4,481,177, 4,556,477 and European Patent No. 102,716, the entire contents of each being expressly incorporated herein by reference.

ZSM-23 is more particularly described in U.S. Pat. No. 4,076,842, the entire contents of which are incorporated herein by reference.

ZSM-35 is more particularly described in U.S. Pat. No. 4,016,245, the entire contents of which are incorporated herein by reference.

ZSM-38 is more particularly described in U.S. Pat. No. 4,046,859, the entire contents of which are incorporated herein by reference.

ZSM-48 is more particularly described in U.S. Pat. No. 4,397,827 the entire contents of which are incorporated herein by reference.

Of these, ZSM-5, ZSM-11, ZSM-22 and ZSM-23 are preferred. ZSM-5 is most preferred for use in the catalyst of the present invention.

Additionally, zeolites SSZ-20 and SSZ-23 are preferred. SSZ-20 is disclosed in U.S. Pat. No. 4,483,835, and SSZ-23 is disclosed in U.S. Pat. No. 4,859,442, both of which are incorporated herein by reference.

The crystalline silicate may be in the form of a borosilicate, where boron replaces at least a portion of the aluminum of the more typical aluminosilicate form of the silicate. Borosilicates are described in U.S. Pat. Nos. 4,268,420; 4,269,813; and 4,327,236 to Klotz, the disclosures of which patents are incorporated herein by reference, particularly that disclosure related to borosilicate preparation.

In the borosilicate used in the process and catalyst of the present invention, the preferred crystalline structure is that of ZSM-5, in terms of X-ray diffraction pattern. Boron in the ZSM-5 type borosilicates takes the place of aluminum that is present in the more typical ZSM-5 crystalline aluminosilicate structures. Borosilicates contain boron in place of aluminum, but generally there is some trace amounts of aluminum present in crystalline borosilicates.

Still further crystalline silicates which can be used in the present invention are ferrosilicates, as disclosed for example in U.S. Pat. No. 4,238,318, gallosilicates, as disclosed for example in U.S. Pat. No. 4,636,483, and chromosilicates, as disclosed for example in U.S. Pat. No. 4,299,808.

Thus, various high silica content silicates (silicates having a high ratio of silica to other constituents) can be used as the zeolite component of the catalyst of the present invention.

Borosilicates and aluminosilicates are preferred silicates for use in the present invention. Aluminosilicates are the most preferred. Silicalite is a particularly preferred aluminosilicate for use in the catalyst of the present invention.

As synthesized, silicalite (according to U.S. Pat. No. 4,061,724) has a specific gravity at 77° F. of 1.99±0.05 g/cc as measured by water displacement. In the calcined form (1112° F. in air for one hour), silicalite has a specific gravity of 1.70±0.05 g/cc. With respect to the mean refractive index of silicalite crystals, values obtained by measurement of the as synthesized form and the calcined form (1112° F. in air for one hour) are 1.48±0.01 and 1.39±0.01, respectively.

The X-ray powder diffraction pattern of silicalite (1112° F. calcination in air for one hour) has six relatively strong lines (i.e., interplanar spacings). They are set forth in Table 2 ("S"-strong, and "VS"-very strong):

TABLE 2

| d-A | Relative Intensity |
| --- | --- |
| 11.1 ± 0.2 | VS |
| 10.0 ± 0.2 | VS |
| 3.85 ± 0.07 | VS |
| 3.82 ± 0.07 | S |
| 3.76 ± 0.05 | S |
| 3.72 ± 0.05 | S |

Table 3 shows the X-ray powder diffraction pattern of a typical silicalite composition containing 51.9 moles of $SiO_2$ per mole of tetrapropyl ammonium oxide [$(TPA)_2O$], prepared according to the method of U.S. Pat. No. 4,061,724, and calcined in air at 1112° F. for one hour.

TABLE 3

| d-A | Relative Intensity |
| --- | --- |
| 11.1 | 100 |
| 10.02 | 64 |
| 9.73 | 16 |
| 8.99 | 1 |
| 8.04 | 0.5 |
| 7.42 | 1 |
| 7.06 | 0.5 |
| 6.68 | 5 |
| 6.35 | 9 |
| 5.98 | 14 |
| 5.70 | 7 |
| 5.57 | 8 |
| 5.36 | 2 |
| 5.11 | 2 |
| 5.01 | 4 |

TABLE 3-continued

| d-A | Relative Intensity |
|---|---|
| 4.98 | 5 |
| 4.86 | 0.5 |
| 4.60 | 3 |
| 4.44 | 0.5 |
| 4.35 | 5 |
| 4.25 | 7 |
| 4.08 | 3 |
| 4.00 | 3 |
| 3.85 | 59 |
| 3.82 | 32 |
| 3.74 | 24 |
| 3.71 | 27 |
| 3.64 | 12 |
| 3.59 | 0.5 |
| 3.48 | 3 |
| 3.44 | 5 |
| 3.34 | 11 |
| 3.30 | 7 |
| 3.25 | 3 |
| 3.17 | 0.5 |
| 3.13 | 0.5 |
| 3.05 | 5 |
| 2.98 | 10 |

Silicalite crystals in both the "as synthesized" and calcined forms are generally orthorhombic and have the following unit cell parameters: a=20.05 A, b=19.86 A, c=13.36 A (all values ±0.1 A).

The pore diameter of silicalite is about 6 Å and its pore volume is 0.18 cc/gram as determined by adsorption. Silicalite adsorbs neopentane (6.2 A kinetic diameter) slowly at ambient room temperature. The uniform pore structure imparts size-selective molecular sieve properties to the composition, and the pore size permits separation of p-xylene from o-xylene, m-xylene and ethyl-benzene as well as separations of compounds having quaternary carbon atoms from those having carbon-to-carbon linkages of lower value (e.g., normal and slightly branched paraffins).

The crystalline silicates of U.S. Pat. No. Res. 29,948 (Reissue of U.S. Pat. No. 3,702,886 to Argauer) are disclosed as having a composition, in the anhydrous state, as follows:

$0.9\pm0.2$ [$xR_2O+(1-x)M_{2/n}O$]:<0.005
$Al_2O_3$:>1 $SiO_2$ where M is a metal, other than a metal of Group IIIA, n is the valence of said metal, R is an alkyl ammonium radical, and x is a number greater than 0 but not exceeding 1. The crystalline silicate is characterized by the X-ray diffraction pattern of Table 1, above.

The crystalline silicate polymorph of U.S. Pat. No. 4,073,865 to Flanigen et al. is related to silicalite and, for purposes of the present invention, is regarded as being in the ZSM-5 class. The crystalline silicate exhibits the X-ray diffraction pattern of Table 4.

TABLE 4

| d(A) | Intensity |
|---|---|
| 11.14 | 91 |
| 10.01 | 100 |
| 9.75 | 17 |
| 8.99 | 1 |
| 8.01 | 0.5 |
| 7.44 | 0.5 |
| 7.08 | 0.2 |
| 6.69 | 4 |
| 6.36 | 6 |
| 5.99 | 10 |
| 5.71 | 5 |
| 5.57 | 5 |
| 5.37 | 1 |
| 5.33 | 1 |
| 5.21 | 0.3 |
| 5.12 | 1.5 |
| 5.02 | 3 |
| 4.97 | 6 |
| 4.92 | 0.6 |
| 4.72 | 0.5 |
| 4.62 | 2 |
| 4.47 | 0.6 |
| 4.36 | 3 |
| 4.25 | 4 |
| 4.13 | 0.5 |
| 4.08 | 1.5 |
| 4.00 | 3 |
| 3.85 | 44 |
| 3.82 | 25 |
| 3.71 | 21 |
| 3.65 | 5 |
| 3.62 | 5 |
| 3.59 | 1 |
| 3.48 | 1.5 |
| 3.45 | 3 |
| 3.44 | 3 |
| 3.35 | 3 |
| 3.31 | 5 |
| 3.25 | 1.5 |
| 3.23 | 0.8 |
| 3.22 | 0.5 |

For purposes of the present invention, silicalite is regarded as being in the ZSM-5 class, alternatively put, as being a form of ZSM-5 having a very high silica to alumina ratio; silicalite-2 is regarded as being in the ZSM-11 class.

The preparation of zeolites of the present invention generally involves the hydrothermal crystallization of a reaction mixture comprising water, a source of silica, and an organic templating compound at a pH of 10 to 14. Representative templating moieties include quaternary cations such as $XR_4$ where X is phosphorous or nitrogen and R is an alkyl radical containing from 2 to 6 carbon atoms, e.g., tetrapropylammonium hydroxide (TPA-OH) or halide, as well as alkyl hydroxyalkyl compounds, organic amines and diamines, and heterocycles such as pyrrolidine.

When the organic templating compound (i.e., TPA-OH) is provided to the system in the hydroxide form in sufficient quantity to establish a basicity equivalent to the pH of 10 to 14, the reaction mixture may contain only water and a reactive form of silica as additional ingredients. In those cases in which the pH must be increased to above 10, ammonium hydroxide or alkali metal hydroxides can be suitably employed for that purpose, particularly the hydroxides of lithium, sodium and potassium. The ratio: $R^+$ to the quantity $R^+$ plus $M^+$, where $R^+$ is the concentration of organic templating cation and $M^+$ is the concentration of alkali metal cation, is preferably between 0.7 and 0.98, more preferably between 0.8 and 0.98, most preferably between 0.85 and 0.98.

The source of silica in the reaction mixture can be wholly, or in part, alkali metal silicate. Other silica sources include solid reactive amorphous silica, e.g., fumed silica, precipitated silica, silica sols, silica gel, and organic orthosilicates. One commercial silica source is Ludox AS-30, available from Du Pont.

Aluminum, usually in the form of alumina, is easily incorporated as an impurity into the zeolite. Aluminum in the zeolite contributes acidity to the catalyst, which is undesirable. To minimize the amount of aluminum, care should be exercised in selecting a silica source with a minimum aluminum content. Commercially available silica sols can typically contain between 500 and 700 ppm alumina, whereas fume silicas can contain between 80 and 2000 ppm of alumina impurity. As explained above, the silica to alumina molar ratio in the zeolite of the catalyst used in the present invention is preferably greater than 30:1, more preferably greater than 200:1, most preferably greater than 500:1.

The quantity of silica in the reaction system is preferably between about 1 and 10 moles $SiO_2$ per mole-ion of the organic templating compound. Water should be generally present in an amount between 10 and 700 mole per mole-ion of the quaternary cation. The reaction preferably occurs in an aluminum-free reaction vessel which is resistant to alkali or base attack, e.g., Teflon.

In forming the final catalyst used in the present invention, the zeolite is preferably bound with a matrix. The term "matrix" includes inorganic compositions with which the silicate can be combined, dispersed, or otherwise intimately admixed. Preferably, the matrix is not catalytically active in a hydrocarbon cracking sense, i.e., contains substantially no acid sites. Satisfactory matrices include inorganic oxides. Preferred inorganic oxides include alumina, silica, naturally occurring and conventionally processed clays, for example bentonite, kaolin, sepiolite, attapulgite and halloysite. Preferred matrices are substantially non-acidic and have little or no cracking activity. Silica matrices and also alumina matrices are especially preferred. We have found that the use of a low acidity matrix, more preferably a substantially non-acidic matrix, is advantageous in the catalyst of the present invention.

Compositing the zeolite with an inorganic oxide matrix can be achieved by any suitable method wherein the zeolite is intimately admixed with the oxide while the latter is in a hydrous state (for example, as a hydrous salt, hydrogel, wet gelatinous precipitate, or in a dried state, or combinations thereof). A convenient method is to prepare a hydrous mono or plural oxide gel or cogel using an aqueous solution of a salt or mixture of salts (for example, aluminum sulfate and sodium silicate). Ammonium hydroxide carbonate (or a similar base) is added to the solution in an amount sufficient to precipitate the oxides in hydrous form. Then, the precipitate is washed to remove most of any water soluble salts and it is thoroughly admixed with the zeolite which is in a finely divided state. Water or a lubricating agent can be added in an amount sufficient to facilitate shaping of the mix (as by extrusion).

A preferred zeolite for use in the catalyst of the present invention is ZSM-5 having a very high silica to alumina ratio, which, for convenience, is frequently referred to herein as "silicalite". Assuming that the only crystalline phase in the silicalite prep is silicalite, the silicalite preferably has a percent crystallinity of at least 80%, more preferably at least 90%, most preferably at least 95%. To determine percent crystallinity, an X-ray diffraction (XRD) pattern of the silicalite is made and the area under the eight major peaks is measured in the angle interval between 20.5 and 25.0 degrees. Once the area under the curve is calculated, it is compared with the area under the curve for a 100% crystalline standard for silicalite.

The preferred crystallite size of the zeolite is less than 10 microns, more preferably less than 5 microns, still more preferably less than 2 microns, and most preferably less than 1 micron. When a crystallite size is specified, preferably at least 70 wt. % of the crystallites are that size, more preferably at least 80 wt % most preferably 90 wt. %. Crystallite size can be controlled by adjusting synthesis conditions, as known to the art. These conditions include temperature, pH, and the mole ratios $H_2O/SiO_2$, $R^+/SiO_2$, and $M^+/SiO_2$, where $R^+$ is the organic templating cation and $M^+$ an alkali metal cation. For small crystallite size, i.e., less than 10 microns, typical synthesis conditions are listed below:

|  | Preferred | More Preferred | Most Preferred |
| --- | --- | --- | --- |
| Temperature, °F. | 176–392 | 194–356 | 212–302 |
| pH | 12–14 | 12.5–14 | 13–13.5 |
| $H_2O/SiO_2$ | 5–100 | 5–50 | 5–40 |
| $R^+/SiO_2$ | 0.1–1.0 | 0.1–0.5 | 0.2–0.5 |
| $M^+/SiO_2$ | 0.01–0.3 | 0.01–0.15 | 0.01–0.08 |

Other techniques known to the art, such as seeding with zeolite crystals, can be used to reduce crystallite size. The zeolite component of the catalyst of the present invention has an intermediate pore size. By "intermediate pore size" as used herein is meant an effective pore aperture in the range of about 5 to 6.5 Angstroms when the zeolite is in the H-form. Zeolites having pore apertures in this range tend to have unique molecular sieving characteristics. Unlike small pore crystalline silicates or zeolites such as erionite, they will allow hydrocarbons having some branching into the zeolitic void spaces. Unlike large pore zeolites such as the faujasites, they can differentiate between n-alkanes and slightly branched alkanes on the one hand and larger branched alkanes having, for example, quaternary carbon atoms.

The effective pore size of the crystalline silicates or zeolites can be measured using standard adsorption techniques and hydrocarbonaceous compounds of known minimum kinetic diameters. See Breck, *Zeolite Molecular Sieves,* 1974 (especially Chapter 8) and Anderson et al., J. Catalysis 58, 114 (1979), both of which are incorporated by reference.

Intermediate pore size crystalline silicates or zeolites in the H-form will typically admit molecules having kinetic diameters of 5 to 6 Angstroms with little hindrance. Examples of such compounds (and their kinetic diameters in Angstroms) are: n-hexane (4.3), 3-methylpentane (5.5), benzene (5.85), and toluene (5.8). Compounds having kinetic diameters of about 6 to 6.5 Angstroms can be admitted into the pores, depending on the particular zeolite, but do not penetrate as quickly and in some cases, are effectively excluded (for example, 2,2-dimethylbutane is excluded from H-ZSM5). Compounds having kinetic diameters in the range of 6 to 6.5 Angstroms include: cyclohexane (6.0), m-xylene (6.1) and 1,2,3,4-tetramethylbenzene (6.4). Generally, compounds having kinetic diameters of greater than about 6.5 Angstroms cannot penetrate the pore apertures and thus cannot be adsorbed in the interior of the zeolite. Examples of such larger compounds include: o-xylene (6.8), hexamethylbenzene (7.1), 1,3,5-trimethylbenzene (7.5), and tributylamine (8.1).

The preferred effective pore size range is from about 5.3 to about 6.2 Angstroms. ZSM-5, ZSM-11 and silicalite, for example, fall within this range.

In performing adsorption measurements to determine pore size, standard techniques are used. It is convenient to consider a particular molecule as excluded if it does not reach at least 95% of its equilibrium adsorption value on the zeolite in less than about 10 minutes (P/Po=0.5 25° C.).

Examples of intermediate pore size zeolites include silicalite and members of the ZSM series such as ZSM-5, ZSM-11, ZSM-12, ZSM21, ZSM-22, ZSM-23, ZSM-35, ZSM-38, SSZ-20 and SSZ-23.

The catalysts according to the present invention contain one or more noble metals. Preferred metals are rhodium, palladium, iridium or platinum. Palladium, and platinum are more preferred. Platinum is most preferred. The preferred percentage of the noble metal, such as platinum, in the catalyst is between 0.1 wt % and 5 wt % from 0.3 wt. % to 2.5 wt. %.

Noble metals are preferably introduced into the zeolite by impregnation, occlusion, or exchange in an aqueous solution or exchange in an aqueous solution of an appropriate salt.

When it is desired to introduce two Group VIII metals into the zeolite, the operation may be carried out simultaneously or sequentially. Preferably, the Group VIII metal is finely dispersed within, and on, the zeolite.

By way of example, platinum can be introduced by impregnation with an aqueous solution of tetraammineplatinum (II) nitrate, tetraammineplatinum (II) hydroxide, dinitrodiamino-platinum or tetraammineplatinum (II) chloride. In an ion exchange process, platinum can be introduced by using cationic platinum complexes such as tetraammineplatinum (II) nitrate or chloride. When platinum is introduced into the zeolite by occlusion, a platinum complex is preferably introduced into the zeolite during its formation.

After platinum impregnation, the catalyst is preferably ammonium exchanged, if necessary, to remove alkali metals.

After the desired metal or metals have been introduced, the catalyst is preferably treated in air, or air diluted with an inert gas, and reduced in hydrogen. Catalysts containing platinum can be subjected to halogen or halide treatments to achieve or maintain a uniform metal dispersion. Typically, the halide is a chloride compound. The catalysts of our invention can be subjected to similar treatments although the preferred catalyst does not contain chloride in the final form.

The catalyst can be employed in any of the conventional types of catalytic dehydrogenation equipment. The catalyst can be employed in the form of pills, pellets, granules, broken fragments, or various special shapes within a reaction zone.

The light paraffinic hydrocarbon feed to the dehydrogenation zone is preferably a light hydrocarbon or naphtha fraction, preferably boiling below about 450° F., more preferably below about 250° F, and most preferably below about 150° F. This can include, for example, straight run naphthas, paraffinic raffinates from aromatic extraction, essentially pure $C_3$, $C_4$, $C_5$ streams or mixtures thereof, and $C_2$–$C_{10}$ paraffin-rich feeds, as well as paraffin-containing naphtha products from other refinery processes, such as hydrocracking or conventional reforming. The feed will preferably contain at least one of propane, butane, isobutane, or a mixture thereof. Preferably, paraffin-rich feeds contain greater than 0.5 wt % $C_2$–$C_{10}$ parrafins, and more preferably grater than 0.5 wt % $C_2$–$C_5$ parrafins. The actual dehydrogenation conditions will depend in large measure on the feed used, whether highly aromatic, paraffinic or naphthenic.

The feed may also contain unreactive gases (e.g. $N_2$ or methane) which can serve to reduce the reactant hydrocarbon partial pressures, thereby resulting in a more favorable thermodynamic equilibrium and greater conversion.

We have found that the catalyst of the present invention has greater stability (for yield) if the amount of water introduced to the reaction zone is less than 50 ppm by weight, more preferably less than 25 ppm.

In the process of the present invention, the pressure is preferably between subatmospheric and 100 psig, more preferably between subatmospheric and 25 psig, and most preferably between subatmospheric and 10 psig. The liquid hourly space velocity (LHSV-calculated on the basis of the volume amount, as a liquid at standard conditions, of hydrocarbon charged to the dehydrogenation zone per hour divided by the volume of the catalyst bed utilized) is preferably between about 0.1 to about 20 hr.$^{-1}$ with a value in the range of about 0.3 to about 5 hr.$^{-1}$ being preferred. The temperature is preferably between about 700° F. and about 1300° F., more preferably between about 800° F. and about 1100° F. and most preferably between about 800° F. and 1000° F. As is well known to those skilled in the dehydrogenation art, the initial selection of the temperature within this broad range is made primarily as a function of the desired conversion level of the paraffinic hydrocarbon considering the characteristics of the feed and of the catalyst. Thereafter, to provide a relatively constant value for conversion, the temperature is slowly increased during the run to compensate for the inevitable deactivation that occurs.

In accordance with one embodiment of the present invention, the dehydrogenation process is carried out in the absence of added hydrogen. This favors increased yield of product olefins, and allows the dehydrogenation process to be operated at a lower temperature. In accordance with another embodiment of the present invention, the dehydrogenation process is carried out in the presence of recycle hydrogen. This increases catalyst life and conserves heat. The preferred recycle hydrogen to fresh feed hydrocarbon mole ratio is generally in the range between (0–5):1, more preferably (0–2):1, and most preferably (0–1):1. In accordance with the embodiment wherein hydrogen is recycled, the preferred ranges are as stated except with a lower limit of 0.1 recycle hydrogen to fresh feed hydrocarbon mole ratio.

We have found that the catalysts of the present invention achieve particularly good selectivity to olefin production if they are presulfided prior to use in dehydrogenation. The sulfiding of the catalyst can be carried out in situ (in the dehydrogenation reactor or reactors) or ex situ. Preferably, the sulfiding is carried out in situ. Sulfiding techniques known in the art are suitable.

In the process embodiment of the present invention, the hydrocarbon feed is contacted with the catalyst as described above in a dehydrogenation zone or dehydrogenation reactor under dehydrogenation conditions. This contacting can be accomplished by using the catalyst in a fixed-bed system, a moving bed system, a fluidized system or in a batch-type operation; however, it is preferred to use either a fixed-bed system or a dense phase moving bed system.

In a fixed-bed system, typically the hydrocarbon feed is preheated to the desired reaction temperature and then passes into a dehydrogenation zone containing a fixed-bed of the catalyst. The process of the present invention can comprise the use of the catalyst as described above in one or more of the reactors in a series of dehydrogenation reactors or in a dehydrogenation zone which is simply a part of the overall train of reactors used in a dehydrogenation unit.

When the present process is conducted in a series of dehydrogenation reactors, each reactor after the first is preferably maintained at a higher average temperature than the temperature of the preceding reactor. It is more preferred to maintain each reactor after the first at least 10° F., and most preferred at least 20° F. in temperature higher than the preceding reactor in the series.

We have found that the catalyst of the present process may be rejuvenated to at least partially recover activity lost during use in the dehydrogenation process. Rejuvenation is typically conducted by flowing hydrogen over the catalyst in the substantial absence of a hydrocarbon feed at a temperature between about 1000° F. and about 1200° F. for between about 4 hours and about 48 hours, and preferably for between about 8 hours and about 24 hours. It has also been found that the catalyst is most effectively rejuvenated when the rate of catalyst deactivation during dehydrogenation is maintained at low levels, for example by restricting the reaction temperature of the dehydrogenation process to a maximum of at most about 1000° F. By a "substantial absence of hydrocarbon feed" is meant that hydrocarbon is not introduced to the catalyst during rejuvenation. Typically, liquid hydrocarbons are drained from the dehydrogenation reactor before rejuvenation, but it is not required that residual liquid remaining on the catalyst after the liquid is drained be flushed from the catalyst before rejuvenation.

In a separate embodiment of the invention, the present dehydrogenation process may be operated in combination with a process for separating hydrogen from the dehydrogenation reaction zone effluent. Processes available to the art for separating hydrogen from liquid and/or gaseous hydrocarbon streams are useful in the present process. These include distillation, adsorption, absorption, extraction, and permeation through a semipermeable membrane. J. N. Armor, *Applied Catalysis*, 49, 1 (89) describes separation processes for recovering a purified hydrogen stream from hydrogen/hydrocarbon mixtures using a semipermeable membrane. Thus, a dehydrogenation reaction zone effluent comprising hydrogen and hydrocarbons may be contacted with a semipermeable membrane which preferentially allows the passage of hydrogen through the membrane. A non-limiting example of such a membrane is a metal or metal alloy of high permeability to hydrogen (e.g. Pd, Pd/Ag), either alone as a thin foil or as a thin film on a support also permeable to hydrogen (e.g. porous ceramic, glass). Non-metallic inorganic membranes and polymer membranes are also known to the art.

The product streams following hydrogen separation are a olefin-enriched hydrocarbon stream and a hydrogen-rich stream. The olefin-enriched hydrocarbon stream may be contacted in a second (or subsequent if more than two dehydrogenation reaction zones are employed) dehydrogenation reaction zone with a dehydrogenation catalyst. The hydrogen-rich stream may be recycled to one or more of the dehydrogenation reaction zones, or it may be used elsewhere.

EXAMPLES

Comparative Example A (This example demonstrates that the use of silicalite which is free of alkali as claimed in U.S. Pat. No. 4,795,732 can give excessive cracking, lowering selectivity and product value.)

One gram of $NaNO_3$ was dissolved in 20 grams of distilled $H_2O$. To this was added 288 grams of a 1M aqueous solution of tetrapropylammonium hydroxide (TPAOH) with mixing. 166 grams of a 30% silica sol (Ludox AS-30) were then added and mixed for 10 minutes. The mixture was then placed in a sealed Teflon bottle and heated for 7 days at 100° C. The product was centrifuged, the supernatant removed, and the solids washed with distilled water, dried overnight in a vacuum oven at 110° C., and calcined in dry air for 8 hours at 538° C. The solid product was identified as 100% silicalite by X-ray diffraction analysis. The average particle size, as determined by scanning electron microscopy (SEM), was about 0.4 microns. Chemical analysis by the Inductively Coupled Plasma technique (using a Model 3580 ICP sold by Applied Research Laboratories, Calif.) showed the sieve to contain 900 ppm Al. At this Al content, the $SiO_2/Al_2O_3$ molar ratio was about 1000. The sieve was then impregnated with 0.8% Pt using an aqueous solution of $Pt(NH_3)_4(NO_3)_2$ and the pore-fill method, then dried overnight in a vacuum oven at 110° C. and calcined in dry air for 8 hours at 260° C. The catalyst was then exchanged twice at 80° C. using a 25% aqueous solution of ammonium acetate, filtered, then dried for 8 hours in a vacuum oven at 110° C., and calcined in dry air for 2 hours at 204° C. The calcined catalyst was found by ICP to contain 50 ppm Na, for an alkali/aluminum molar ratio of 0.07.

The catalyst was then tested for dehydrogenation in a fixed-bed reactor in a pilot plant equipped with a gas chromatograph. The catalyst was reduced in hydrogen at 482° C. for 2 hours, presulfided at that temperature with dimethyldisulfide (DMDS) at the ratio of 2 moles S per mole Pt, then used to dehydrogenate isobutane at 428° C., atmospheric pressure, and 5 LHSV with no added hydrogen. Isobutane conversion was 50% but selectivity to isobutene was only 27%. Selectivity to lower valued cracked product was 25%, with most of the remainder to isomerized $C_4$'s.

Comparative Example B (This example demonstrates that use of a high alkali silicate as claimed in U.S. Pat. No. 4,438,288 gives very little conversion in the process.)

11.5 grams of $NaNO_3$ were dissolved in 50 grams of distilled $H_2O$. 500 grams of a 25% aqueous solution of TPAOH were added and mixed for 5 minutes. 5 grams of $H_3BO_3$ were then added with mixing, followed by 400 grams of Ludox AS-30 and mixed for 15 minutes. The mixture was placed in a sealed Teflon bottle and heated at 90° C. for 5 days. The product was then centrifuged, the supernatant removed, and the solids washed with distilled water. The solids were dried overnight in a vacuum over at 110° C. and then calcined in dry air for 8 hours at 538° C. The solids were identified as 100% silicalite by X-ray diffraction analysis. The average particle size, as determined by SEM, was about 0.3 microns. ICP analysis showed the sieve to contain 766 ppm Al and 1% Na, for an alkali/Al molar ratio of about 15. The sieve was then impregnated with 0.8% Pt using an aqueous solution of $Pt(NH_3)_4(NO_3)_2$ by the pore-fill method, dried overnight in a vacuum oven at 110° C., the calcined in dry air for 8 hours at 260° C.

The catalyst was then reduced, presulfided, and tested for isobutane dehydrogenation as the catalyst in Comparative Example A. Conversion was less than 3%.

Example 1

80 grams of $NaNO_3$ were dissolved in 80 grams of distilled $H_2O$. 8.3 grams of $H_3BO_3$ were added with mixing, followed by 800 grams of a 25% aqueous solution of TPAOH and mixed for 10 minutes. 200 additional grams of 25% TPAOH and 800 grams of $H_2O$ were then added with mixing. Then 200 grams of a fumed silica (Cab-O-Sil M-5) were added and mixed for 10 minutes. The mixture was placed in a sealed Teflon bottle and heated at 100° C. for 7 days. The product was centrifuged, the supernatant removed, and the solids washed with distilled water. The solids were dried overnight in a vacuum oven at 110° C., then calcined in dry air for 8 hours at 538° C. The solids were identified as 100% silicalite by X-ray diffraction analysis. The average particle diameter, as determined by SEM, was about 0.5 microns. The catalyst was impregnated with 0.8% Pt using an aqueous solution of $Pt(NH_3)_4(NO_3)_2$ and the pore-fill method. The catalyst was dried overnight in a vacuum oven at 110° C., then calcined in dry air at 177° C. for 4 hours, 232° C. for 4 hours, and 288° C. for 4 hours. It was then exchanged twice at 80° C. using a 25% aqueous solution of ammonium acetate, filtered, then dried in a vacuum oven overnight at 110° C. The catalyst was then impregnated with 0.05% Na using an aqueous solution of $Na_2CO_3$ and the pore-fill method, then dried overnight in a vacuum oven at 110° C. and calcined in dry air for 4 hours at 260° C. The catalyst contained 264 ppm Al by ICP analysis, and had an alkali/Al molar ratio of about 2.

The catalyst was then reduced, presulfided, and tested for isobutane dehydrogenation as the catalyst in Comparative Example A. Conversion was 29% with 70% selectivity to isobutene.

Example 2

A silicalite sample containing 900 ppm Al was prepared. The sieve was impregnated with 0.3% Na using an aqueous solution of $NaNO_3$ and the pore-fill method. The sieve was dried overnight in a vacuum oven at 110° C. then calcined at 260° C. for 4 hours in dry air. It was then impregnated with 0.8% Pt using an aqueous solution of $Pt(NH_3)_4(NO_3)_2$ and the pore-fill method, dried overnight in a vacuum oven at 110° C., then calcined in dry air at 149° C. for 2 hours, 204° C. for 2 hours, and 288° C. for 4 hours. The catalyst was then impregnated with 0.15% Mg using an aqueous solution of $Mg(NO_3)_2$ and the pore-fill method, then dried and calcined by the same procedure used after Pt impregnation. The alkali/Al molar ratio for this catalyst was about 4.

The catalyst was reduced in hydrogen for 2 hours at 482° C., then presulfided with DMDS. The catalyst was then used to dehydrogenate n-butane at 482° C., 5 LHSV, and atmospheric pressure with no added hydrogen. The catalyst ran at about 21% conversion with 91% selectivity with almost no deactivation over a 380-hour time period.

Example 3

To 100 grams of silica (Hi-Sil 233, a hydrated silica manufactured by PPG) were added 8 grams of kaolin clay powder (53.7 wt. % $SiO_2$, 42.5 wt. % $Al_2O_3$) and 60 grams of a 40 wt % aqueous solution of TPAOH and mixed for 1 hour in a Baker-Perkins mixer. Then 0.34 grams of $H_3BO_3$ were dissolved in 25 grams of water and added to the above mixture along with 5.8 grams of a 50 wt. % aqueous solution of NaOH. Mixing continued for another 30 minutes. The mixture was then extruded through a 1/16-inch die. The extrudate was placed in a sealed Teflon bottle and heated at 100° C. for 4 days. The extrudate was then dried overnight at 110° C. in a vacuum oven and calcined in air at 538° C. for 8 hours. The product was identified as about 100% ZSM-5 by X-ray diffraction analysis, and was composed of particles about 0.2 microns in diameter as determined by SEM. ICP analysis showed the catalyst to contain 1.5% Na and 1.4% Al such that the alkali/Al molar ratio was about 1.3. The catalyst was impregnated with 0.8% Pt using an aqueous solution of $Pt(NH_3)_4(NO_3)_2$ and the pore-fill method. The catalyst was then dried overnight in a vacuum oven at 110° C. and calcined in dry air for 4 hours at 204° C., 4 hours at 260° C., and 4 hours at 288° C.

The catalyst was reduced in hydrogen for 2 hours at 482° C. then presulfided with DMDS. The catalyst was then used to dehydrogenate n-butane at 482° C., 5 LHSV, and atmospheric pressure with no added hydrogen. The catalyst ran at about 24% conversion with 93% selectivity to n-butenes with almost no deactivation over a 480-hour time period.

Example 4

Equal volumes of the fresh catalyst of Example 3 were placed in two separate reactors. The catalyst was again tested for n-butane dehydrogenation as in Example 3, with a 5 overall LHSV. This time, however, the first reactor was run at 482° C. and the second at 510° C. The conversion after the second reactor was around 31% at about 92%–93% selectivity to n-butenes with very little deactivation over a 330-hour time period.

Example 5

The dehydrogenation run with the catalyst of Example 1 was continued until conversion dropped to 23%. Feed was discontinued and the catalyst then stripped with hydrogen for 16 hours at 538° C. The catalyst was then cooled to 482° C., hydrogen addition stopped, and isobutane feed restarted. Conversion returned to 30%.

What is claimed is:

1. A process for dehydrogenating a light paraffinic hydrocarbon feed which comprises contacting the feed under catalytic dehydrogenation conditions with a catalyst comprising:
    (a) a noble metal;
    (b) an intermediate pore size zeolite having a silica to alumina mole ratio of about 30 or greater; and
    (c) an alkali content wherein the alkali to aluminum ratio in the zeolite is between about 1 and about 5 on a molar basis.

2. The process in accordance with claim 1 wherein the silica to alumina mole ratio of the zeolite is at least 200.

3. The process in accordance with claim 1 wherein the silica to alumina mole ratio of the zeolite is at least 500.

4. The process in accordance with claim 1 wherein the alkali to aluminum ratio in the silicate is between about 1 and about 3 on a molar basis.

5. The process in accordance with claim 1 wherein the catalyst is subject to at least periodic exposure in the dehydrogenation zone to more than 500 ppb sulfur.

6. The process in accordance with claim 1 wherein the catalyst is subject to at least periodic exposure in the dehydrogenation zone to more than 1000 ppb sulfur.

7. The process in accordance with claim 1 wherein the catalyst is presulfided.

8. The process in accordance with claim 3 wherein the catalyst is presulfided.

9. The process in accordance with claim 4 wherein the catalyst is presulfided.

10. The process in accordance with claim 1 wherein the zeolite crystallite size is less than 5 microns.

11. The process in accordance with claim 10 wherein the zeolite crystallite size is less than 2 microns.

12. The process in accordance with claim 11 wherein the catalyst is presulfided or sulfided.

13. The process in accordance with claim 1 wherein the hydrocarbon feed contains no more than 2 ppm sulfur.

14. The process in accordance with claim 1 wherein the hydrocarbon feed contains between 0.01 and 2 ppm sulfur.

15. The process in accordance with claim 1 wherein the zeolite is ZSM-5.

16. The process in accordance with claim 1 wherein the zeolite is ZSM-11.

17. The process in accordance with claim 1 wherein the noble metal is platinum, palladium, iridium or rhodium.

18. The process in accordance with claim 1 wherein the noble metal is platinum.

19. The process in accordance with claim 1 wherein the light paraffinic hydrocarbon feed comprises at least one of propane, butane, isobutane, or a mixture thereof.

20. The process in accordance with claim 1 wherein the reaction zone comprises a multiplicity of dehydrogenation reactors.

21. The process in accordance with claim 20 wherein each reactor after the first is maintained at an average temperature higher than the average temperature of the preceding reactor.

22. The process in accordance with claim 1 further comprising the step of rejuvenating the catalyst.

23. The process in accordance with claim 22 wherein said rejuvenation step is conducted in flowing hydrogen at a temperature in the range from about 1000° F. to about 1200° F.

24. The process in accordance with claim 23 wherein said rejuvenation step is conducted in the substantial absence of hydrocarbon feed.

25. The process in accordance with claim 1 further comprising the step of separating the dehydrogenation reaction zone effluent into a hydrogen-rich stream and an olefin-enriched hydrocarbon stream.

26. The process in accordance with claim 25 wherein said separation step includes contacting the dehydrogenation reaction zone effluent with a semipermeable membrane.

27. The process in accordance with claim 1 wherein the catalyst is subject to at least periodic exposure in the dehydrogenation zone to more than 100 ppb sulfur.

28. A process for dehydrogenating a hydrocarbon feed which comprises contacting the feed under catalytic dehydrogenation conditions with a catalyst comprising:
   (a) a noble metal;
   (b) an intermediate pore size zeolite having a silica to alumina mole ratio of about 200 or greater; and
   (c) an alkali content wherein the alkali to aluminum ratio in the zeolite is between about 1 and about 5 on a molar basis.

29. The process in accordance with claim 28 wherein the silica to alumina mole ratio is at least 500.

30. The process in accordance with claim 28 wherein the catalyst is subject to at least periodic exposure in the dehydrogenation zone to more than 500 ppb sulfur.

31. The process in accordance with claim 28 wherein the catalyst is subject to at least periodic exposure in the dehydrogenation zone to more than 1000 ppb sulfur.

32. The process in accordance with claim 28 wherein the catalyst is presulfided.

33. The process in accordance with claim 29 wherein the catalyst is presulfided.

34. The process in accordance with claim 28 wherein the zeolite crystallite size is less than 5 microns.

35. The process in accordance with claim 34 wherein the zeolite crystallite size is less than 2 microns.

36. The process in accordance with claim 35 wherein the catalyst is presulfided or sulfided.

37. The process in accordance with claim 28 wherein the zeolite is ZSM-5.

38. The process in accordance with claim 28 wherein the zeolite is ZSM-11.

39. The process in accordance with claim 28 wherein the noble metal is platinum, palladium, iridium or rhodium.

40. The process in accordance with claim 28 wherein the noble metal is platinum.

* * * * *